(12) United States Patent
Suehling et al.

(10) Patent No.: US 11,024,000 B2
(45) Date of Patent: Jun. 1, 2021

(54) CONTROLLING A MEDICAL IMAGING SYSTEM

(71) Applicant: Siemens Healthcare GmbH, Erlangen (DE)

(72) Inventors: Michael Suehling, Erlangen (DE); Andreas Wimmer, Forchheim (DE); Christian Petry, Langensendelbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/114,315

(22) Filed: Aug. 28, 2018

(65) Prior Publication Data

US 2019/0066260 A1 Feb. 28, 2019

(30) Foreign Application Priority Data

Aug. 31, 2017 (EP) .................................... 17188840

(51) Int. Cl.
*G06T 3/00* (2006.01)
*G06T 7/593* (2017.01)
(Continued)

(52) U.S. Cl.
CPC .......... *G06T 3/0068* (2013.01); *A61B 5/0077* (2013.01); *A61B 5/744* (2013.01);
(Continued)

(58) Field of Classification Search
None
See application file for complete search history.

(56) References Cited

U.S. PATENT DOCUMENTS 5,539,798 A 7/1996 Asahina et al.
6,081,739 A * 6/2000 Lemchen ............. A61B 5/0064
600/407
(Continued)

FOREIGN PATENT DOCUMENTS

DE 102006001850 A1 8/2007
DE 102013200135 A1 7/2014
(Continued)

OTHER PUBLICATIONS

Extended European Search Report and English translation thereof dated Mar. 26, 2018.
(Continued)

*Primary Examiner* — Michelle M Entezari
(74) *Attorney, Agent, or Firm* — Harness, Dickey & Pierce, P.L.C.

(57) ABSTRACT

In an embodiment, a method includes providing a three-dimensional structure image including surface data relating to external contours and structure data relating to internal structures of a body region; recording the body region via a camera system, to produce a recording while a patient is situated in or on the medical imaging system; registering, at least locally and as a structure image, the three-dimensional surface image in relation to the three-dimensional structure image; producing an overlay image including at least part of the structure image registered including structure data of the three-dimensional structure image in a form of an overlay with at least one of the three-dimensional surface image and a real view of a corresponding part of the body region of the patient; and controlling the medical imaging system to record body regions of the patient based upon an arrangement of the structure data registered in the overlay image.

24 Claims, 4 Drawing Sheets

(51) Int. Cl.
*G06T 7/73* (2017.01)
*A61B 6/00* (2006.01)
*A61B 5/00* (2006.01)
*G06T 19/00* (2011.01)
*A61B 6/03* (2006.01)
*A61B 90/00* (2016.01)

(52) U.S. Cl.
CPC .............. *A61B 6/032* (2013.01); *A61B 6/461* (2013.01); *A61B 6/463* (2013.01); *A61B 6/5247* (2013.01); *A61B 6/545* (2013.01); *G06T 7/593* (2017.01); *G06T 7/74* (2017.01); *G06T 19/006* (2013.01); *A61B 6/488* (2013.01); *A61B 2090/365* (2016.02); *G06T 2207/10028* (2013.01); *G06T 2207/10081* (2013.01); *G06T 2207/20221* (2013.01); *G06T 2207/30004* (2013.01); *G06T 2207/30208* (2013.01)

(56) References Cited

U.S. PATENT DOCUMENTS

| | | | | |
|---|---|---|---|---|
| 10,832,469 B2* | 11/2020 | Chapman | ............. | G06K 9/4652 |
| 2004/0267113 A1* | 12/2004 | Thomson | ............. | A61N 5/1049 |
| | | | | 600/427 |
| 2007/0172102 A1 | 7/2007 | Hempel | | |
| 2014/0163375 A1* | 6/2014 | Wasielewski | ........ | A61B 8/4427 |
| | | | | 600/443 |
| 2015/0104092 A1 | 4/2015 | Flohr et al. | | |
| 2015/0157267 A1* | 6/2015 | Shushan | ............. | A61B 5/6885 |
| | | | | 600/407 |
| 2015/0223902 A1* | 8/2015 | Walker | ............. | A61B 17/12118 |
| | | | | 600/424 |
| 2015/0348247 A1* | 12/2015 | McLaughlin | ............. | G06T 3/40 |
| | | | | 382/131 |
| 2016/0191887 A1* | 6/2016 | Casas | ................... | H04N 13/296 |
| | | | | 348/47 |
| 2017/0224298 A1 | 8/2017 | Hannemann et al. | | |
| 2018/0055468 A1* | 3/2018 | Reicher | .................. | A61B 6/468 |
| 2018/0218501 A1* | 8/2018 | Hillborg | ............. | A61N 5/1084 |
| 2018/0235573 A1* | 8/2018 | Langeland | ........... | A61B 8/0841 |
| 2018/0235701 A1* | 8/2018 | Gerard | ................. | A61B 6/5229 |

FOREIGN PATENT DOCUMENTS

| | | |
|---|---|---|
| DE | 102013220665 A1 | 4/2015 |
| DE | 102014216718 A1 | 2/2016 |

OTHER PUBLICATIONS

European Intention to Grant and English translation thereof dated Sep. 13, 2019.
Extended European Search Report #17188840.7 dated Mar. 26, 2018.

* cited by examiner

CONTROLLING A MEDICAL IMAGING SYSTEM

PRIORITY STATEMENT

The present application hereby claims priority under 35 U.S.C. § 119 to European patent application number EP17188840.7 filed Aug. 31, 2017, the entire contents of which are hereby incorporated herein by reference.

FIELD

Embodiments of the invention generally relate to a method and a control device for controlling a medical imaging system, and to a medical imaging system having such a control device.

BACKGROUND

Medical imaging such as computer tomography or magnetic resonance tomography is routinely used in the diagnosis of illnesses, particularly for treatment or for monitoring the progress of therapy. Patients are usually scanned several times in this case. Following a cancer diagnosis, for example, medical recordings of a patient are produced several times during the course of therapy (e.g. using a computer tomograph "CT") in order to monitor the progression of the illness. When preparing a medical image recording, it is important to know the site and extent of the internal region to be examined, e.g. in order to select a suitable position or pose of the patient on the table.

In order to prepare a medical image recording, external body features are often used in order to approximately estimate the location of the internal structures. Lasers, e.g. on the gantry of a CT, are used to match the selected region with the scanner coordinates system. The table height is usually selected such that the midpoint of the body surface of the patient is aligned with the isocenter of the gantry. In some cases, planning results are transferred onto the patient using a pen to draw markings on the skin, e.g. insertion points for needles. Use is routinely made of measuring tools such as triangular rulers to approximately orientate medical devices that are to be introduced.

SUMMARY

The inventors have discovered that, at present, the transfer of the aforementioned information to the patient, who is lying on the scanner table, is very difficult. Further, all of the aforementioned is time-intensive and very imprecise because it takes place without the precise knowledge of the current location of the real internal organs, and this represents a significant disadvantage.

Embodiments of the present invention provides a method and a control device for controlling a medical imaging system, by which at least one of the disadvantages described above are avoided.

Embodiments are directed to a method, a control device and a medical imaging system.

An embodiment of the inventive method for controlling a medical imaging system and for localizing internal structures in a predefined body region comprises:

providing a three-dimensional structure image including both surface data relating to external contours and structure data relating to internal structures of a body region;

recording the body region of a patient via a camera system while the patient is situated in or on the medical imaging system, and producing a three-dimensional surface image from the recording;

registering, at least locally and as a structure image, the three-dimensional surface image in relation to the three-dimensional structure image;

producing an overlay image, the overlay image including at least part of the structure image registered including structure data of the three-dimensional structure image in a form of an overlay with at least one of the three-dimensional surface image and a real view of a corresponding part of the body region of the patient; and controlling the medical imaging system to record body regions of the patient based upon an arrangement of the structure data registered in the overlay image.

An embodiment of an inventive control device for controlling a medical imaging system, comprises:

a structure image interface to provide a three-dimensional structure image including surface data relating to external contours and structure data relating to internal structures of a body region of a patient;

a camera system to record at least the body region of the patient in a medical imaging system and to produce recordings;

a surface image production unit designed to produce a three-dimensional surface image from the recordings;

a registration unit to at least locally register, as a structure image, the three-dimensional surface image in relation to the three-dimensional structure image; and an overlay image production unit designed to produce an overlay image, the overlay image including at least part of the structure image registered including registered structure data in a form of an overlay with registered surface image or a real view of a corresponding part of a real body region of the patient, wherein the control device is designed to control the medical imaging system to record regions of the patient based upon an arrangement of the structure data registered in the overlay image At least one embodiment of the application is directed to a medical imaging system, comprising an embodiment of the control device.

At least one embodiment of the application is directed to a non-transitory computer program product storing a computer program, directly loadable into a memory device of a control device, including program sections for executing an embodiment of the method when the computer program is executed in the control device.

At least one embodiment of the application is directed to a non-transitory computer-readable medium storing program sections, readable in and executable by a computer unit, to execute an embodiment of the method when the program sections are executed by the computer unit.

BRIEF DESCRIPTION OF THE DRAWINGS

The invention is explained again in greater detail below with reference to the appended figures and exemplary embodiments. Identical components are denoted by identical reference signs in the various figures. The figures are not generally to scale.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the inventive method for controlling a medical imaging system and for localizing internal structures in a predefined body region comprises:

Providing a Three-Dimensional Structure Image.

This three-dimensional structure image is normally present in the form of three-dimensional image data and comprises both surface data relating to external contours of a specific body region (also referred to as a "region of interest") and structure data relating to internal structures of this body region. The external contours reflect the body surface of the body region concerned. The structure data depicts internal structures, e.g. organs, bones or vessels.

Part of the structure data can preferably be marked as structures of interest, e.g. following the registration. Structures of interest are considered to be those which are preferably to be mapped by the medical imaging system, e.g. because they are of particular interest for the present recording or clinical evaluation to be performed.

However, part of the structure data can preferably also be marked as structures of no interest, e.g. following the registration. Structures of no interest are considered to be those which are not intended to be mapped by the medical imaging system, e.g. because they are of no interest for the present recording or clinical evaluation to be performed, and therefore should not be irradiated in order that the (total) radiation dose is reduced.

Recording (at Least) the Body Region of a Patient.

The patient can be e.g. a person or an animal. The recording is performed by way of a camera system while the patient is situated in the medical imaging system. A three-dimensional surface image of at least the cited body region of the patient is produced from the recordings. The surface image in this case depicts a part of the body surface corresponding to the body region. The recording in this case comprises at least 3D data, but preferably also comprises information in colors or gray tones relating to the body surface of this body region, as explained in greater detail below.

Registering the Surface Image and the Structure Image.

The registration of the surface image and the structure image in relation to each other is done at least locally. The registration can be achieved e.g. with minimization of a cost function, which contains the distances or the inverse squares of previously established corresponding points in the various images relative to each other.

Since in relation to the surface image there is normally no data relating to the true internal structures of the patient, the registration of the surface image with the structure image means that in practice only the surface data of the structure image is used to establish the required graphical transformations for the registration. The internal structure data of the structure image is nonetheless transformed in accordance with the transformation of the surface data that takes place for the registration. This means that the structure image is therefore registered with the surface image by bringing the respective surfaces together in an appropriate manner and adapting at least the above cited structure data in relation thereto, or by transforming the whole structure image accordingly for a required graphical transformation.

As part of the registration, in the case of a transformation of the (preferably whole) structure image, the structure image is therefore mapped onto the surface image in an appropriate manner, wherein the internal structures would then be mapped onto corresponding internal structures (not contained in the surface image) of the patient, with a statistical precision, on the basis of the transformation selected for the registration.

Producing an Overlay Image.

The overlay image in this case comprises at least part of the registered structure image including registered structure data in the form of an overlay with a view of the patient. This can be the registered surface image, in particular if a VR display device is used as described below, and/or a real view of the corresponding part of the real body region, in particular if an AR display device is used as described below.

Controlling the Medical Imaging System.

In this case, the medical imaging system is controlled in such a way that regions of the patient are recorded on the basis of the arrangement of the registered structure data in the overlay image. In this case, it is often not only regions that are important in the context of said control, but also e.g. a slice orientation, a slice distance and/or the number of slices. Control of the slices is therefore also possible on the basis of the overlay image, e.g. by using recording parameters that are specified or automatically generated for various internal structures.

In this case, the medical imaging system is preferably controlled in such a way as to make recordings in at least that region of the patient in which the structure data marked as structures of interest is arranged in the overlay image, and/or so as to make no recordings in at least that region of the patient in which the structure data marked as structures of no interest is arranged in the overlay image. Therefore irradiation selectively does or does not take place in those regions which are highly likely to correspond to the corresponding real structures, depending on the relevance of the structure data for the examination. The expected radiation dose from the recordings is thereby reduced for the patient.

By virtue of the overlay image, this form of control is not difficult to realize. Using the three-dimensional recording of the body region of the patient, the surface image can be unambiguously integrated into the coordinates system of the medical imaging system. Since the structure image including the structure data is registered in the overlay image with the surface image, positioning based of the coordinates system of the medical imaging system is also possible as a function of the registered structure data. Therefore the medical imaging system only has to be controlled within its coordinates system, such that a recording is preferably made selectively for those coordinates at which the registered structures of interest are situated, and/or no recording is preferably made for those coordinates at which the registered structures of no interest are situated.

At least one embodiment of the inventive control device for controlling a medical imaging system comprises the components described below.

A structure image interface for providing a three-dimensional structure image as described above. The structure image comprises both surface data relating to external contours and structure data relating to internal structures of a body region, wherein part of the structure data is preferably marked as structures of interest or no interest by the marking described above.

A camera system for recording at least the body region of the patient in a medical imaging system. Such a camera system can be e.g. a 3D camera, e.g. a depth sensor, possibly interacting with a 2D camera. Preferred camera systems are described in greater detail below.

A surface image production unit, designed to produce a three-dimensional surface image from these recordings as described above.

A registration unit for at least locally (i.e. in those regions of the structures marked as of interest or no interest, for example) registering the surface image and the structure image in relation to each other. This process is likewise described above.

An overlay image production unit which is designed to produce an overlay image, likewise as described above. The overlay image comprises at least part of the registered structure image including registered structure data in the form of an overlay with the registered surface image or the real view of the corresponding part of the real body region.

The control device is designed in this case to control the medical imaging system in such a way that the medical imaging system records regions of the patient on the basis of the arrangement of the registered structure data in the overlay image. Reference is also made to the foregoing description relating to the structures of interest and of no interest.

A medical imaging system according to an embodiment of the invention comprises an embodiment of such an inventive control device.

A large part of the system components cited above can be realized wholly or partly in the form of software modules in a processor of a corresponding control device or computing device. A largely software-based realization has the advantage that an infrastructure which is already in use can also easily be upgraded by way of a software update in order to work in the inventive manner.

To this extent, at least one embodiment of the application is also directed to a computer program product comprising a computer program which can be loaded directly into a memory device of a control device of a medical imaging system, having program sections for executing all steps of embodiments of the inventive method when the program is executed in the control device. Such a computer program product may optionally comprise additional elements in addition to the computer program, e.g. documentation or additional components and even hardware components such as e.g. hardware keys (dongles etc.) for using the software.

At least one embodiment of the application is also directed to a computer-readable medium on which are stored program sections that can be read in and executed by a computer unit in order to execute all steps of embodiments of the inventive method when the program sections are executed by the computer unit.

Further particularly advantageous embodiments and developments of the invention are revealed in the dependent claims and the following description. In this case, the features of embodiment variants in one category can also be used to characterize embodiment variants in another category. For example, the control device according to the invention can also be developed in the same way as the dependent method claims or description parts, wherein the converse also applies correspondingly for the method claims. In particular, individual features of various exemplary embodiments or variants can also be combined to form new exemplary embodiments or variants.

The structure image preferably comprises a medical image recording of the body region of the patient or another patient. The surface data and/or the structure data are preferably images of a real body region in this case.

Likewise, the structure image preferably, alternatively or additionally comprises image data of a body region of an artificially produced avatar. In this case, both the surface data and the internal structures of the avatar are preferably simulated or calculated and correspond to those of a real person or a statistical average over a group of people.

An avatar in this case can represent a virtual body model, e.g. in the form of a geometry and organ-based material properties. An avatar can however also contain statistical model parameters such as e.g. shape variations, material property variations or corresponding variations which are obtained over a group of people, for example.

The three-dimensional surface image is preferably recorded as explained above by way of a depth information sensor, e.g. a 3D camera, and comprises three-dimensional image information relating to the body surface of the patient in respect of at least the predefined body region. The surface image preferably also comprises a patient image made up of two-dimensional grayscale data or color data. A photographic image or film image can then be projected onto the three-dimensional surface, making subsequent registration easier because body features which stand out by virtue of their coloring, e.g. the eyes, can also be used for the registration in addition to the 3D data.

Before the registration, the structure image is preferably automatically aligned and positioned according to the surface image, or a corresponding transformation matrix is generated. This has the advantage that the structure image, e.g. an avatar or the 3D image of the pre-examination, and the surface image of the patient have the same alignment for the subsequent registration, and corresponding body areas such as e.g. stomach, chest or shoulders can easily be registered in relation to each other. This process does not necessarily have to take place during the registration or using a graphical image registration device(s), but can be effected simply by aligning the coordinates system of the structure image according to the coordinates system of the medical imaging system.

A graphical (coordinates) transformation which is applied to the external contours of the structure image for the purpose of registration is preferably also applied to the structure data of the structure image correspondingly. This has the advantage that the internal structures of the structure image, reflecting e.g. organs of the patient, can also be treated independently of the surface data. For example, in the case of an elongation of the surface by X %, the internal structures would also be elongated by X %.

In order to supplement the registration, a patient structure image is preferably also recorded by way of the medical imaging system. This features both internal structures and information relating to the surface of the patient. For example, a "scout scan" (a standard overview recording) could be used as a patient structure image. In this case, the external contour of the patient in the patient structure image preferably corresponds to that in the surface image, i.e. the patient should if possible not move between the recording of the surface image and the patient structure image. In particular, the recording of the patient structure image takes place at the same time as the surface image, thereby minimizing the danger of a movement of the patient and a resulting incongruence between the two recordings.

The patient structure image is preferably registered with the surface image in respect of its information relating to the surface of the patient. Accordingly, the internal structure data of the structure image is also registered with corresponding internal structures of the patient structure image. Regarding this, the registration can be achieved e.g. with minimization of a cost function, which contains the distances or the inverse squares of previously established corresponding points in the various images relative to each other.

For example, a scout scan and a recording of the patient by way of a 3D camera are undertaken first, followed by a registration of scout scan, an avatar and the image recording of the 3D camera. The organs of the avatar are registered with organs of the scout scan in this case.

The overlay image is preferably displayed using a display device. This allows the recording to be checked, and further options which are described in greater detail below. Accordingly, a preferred control device additionally has an interface for such a display device and/or a display device. The display device is preferably a Virtual Reality (VR) display device or an Augmented Reality (AR) display device, e.g. a VR headset or AR headset.

The display of the overlay image can itself be very advantageous for the purpose of control, particularly when functionally combined with an input unit which is designed to record further control data of a user. The input unit can be a simple operating element such as a keyboard or a mouse, for example, but is preferably embodied as a gesture recognition unit or functionally connected to a gesture recognition unit which is capable of recognizing specified gestures of the user and translating these into control instructions. The preferred control device comprises a display device and also an input unit in this case. In order to achieve this, any known methods and devices or software for gesture recognition may be used.

The control data entered by a user by way of the input unit is preferably designed to modify or supplement the control instructions for the recording of regions and/or slices. In addition, control parameters are preferably shown in suitable form in the overlay image. For example, visualizations of the control parameters may be indicators of the region to be recorded, e.g. said region can be specifically identified in the overlay image, or indicators of slices, e.g. the individual slices can be included in the overlay image for this purpose (possibly in color). The control data which is modified or supplemented by the user via the input unit can preferably be displayed in this manner in a newly produced overlay image, for example. If the user repositions the region to be recorded, for example, then this repositioning should be displayed (in real time if applicable) in a new overlay image. It is preferably also possible for the user to orientate slices or slice stacks differently or to modify the slice distance. This likewise should preferably be displayed in the form of a new overlay image.

Provision is preferably made for also determining the position and orientation of the display device, and therefore of the observer likewise, in particular relative to the camera system. This has the advantage that the overlay image can be calculated such that it is represented as seen from the position and orientation of the observer. In this case, the overlay image is preferably displayed in the display device in such a way that the viewing angle from which the overlay image is displayed corresponds to that of the display device onto the patient. For this purpose, the coordinates system of the display device, e.g. an AR or VR headset, is preferably registered with the coordinates system of the camera system or the CT. Marking points in the CT can also be used for this registration, thereby improving the precision, particularly if the display device likewise has cameras which record these marking points.

Markers that are generated automatically from specified data and/or produced manually by a user, e.g. for incisions, punctures or other penetrations, and/or navigation data and/or help data, e.g. labels or outlines of critical body regions, are preferably also represented in the overlay image. This has the advantage, particularly for an examiner or operating surgeon observing the overlay image by way of a display device, that they can plan their next steps more effectively.

The control of the medical imaging system preferably takes place in such a way that the medical imaging system records regions of the patient on the basis of the arrangement of the registered structure data and a marker or a plurality of markers in the overlay image.

Image data relating to a virtual medical object, e.g. needle or endoscope, is preferably represented in the overlay image. The orientation and/or position of the medical object can preferably be changed in this case, e.g. moved, zoomed or rotated. This has the advantage that an optimum procedure for an operation can be simulated virtually.

In addition, the position and/or orientation of the overlay image can preferably be actively changed by the user, e.g. moved, magnified, reduced and/or rotated. This has the advantage that e.g. a view along a needle that must be inserted can be optimally represented. A change of this kind can be achieved by way of simple calculation in the context of a VR representation. In the case of an AR representation, the camera continuously delivers surface images and new overlay images are continuously generated by the method, and therefore the observer can change the viewing direction by way of movement.

The surface image is preferably produced from images which are recorded by way of a 3D camera or by way of a number of 2D cameras that have been interconnected for the purpose of recording a three-dimensional image. In this case, at least one camera is preferably integrated in a display device as described above and/or positioned in the medical imaging system.

Figure 1:
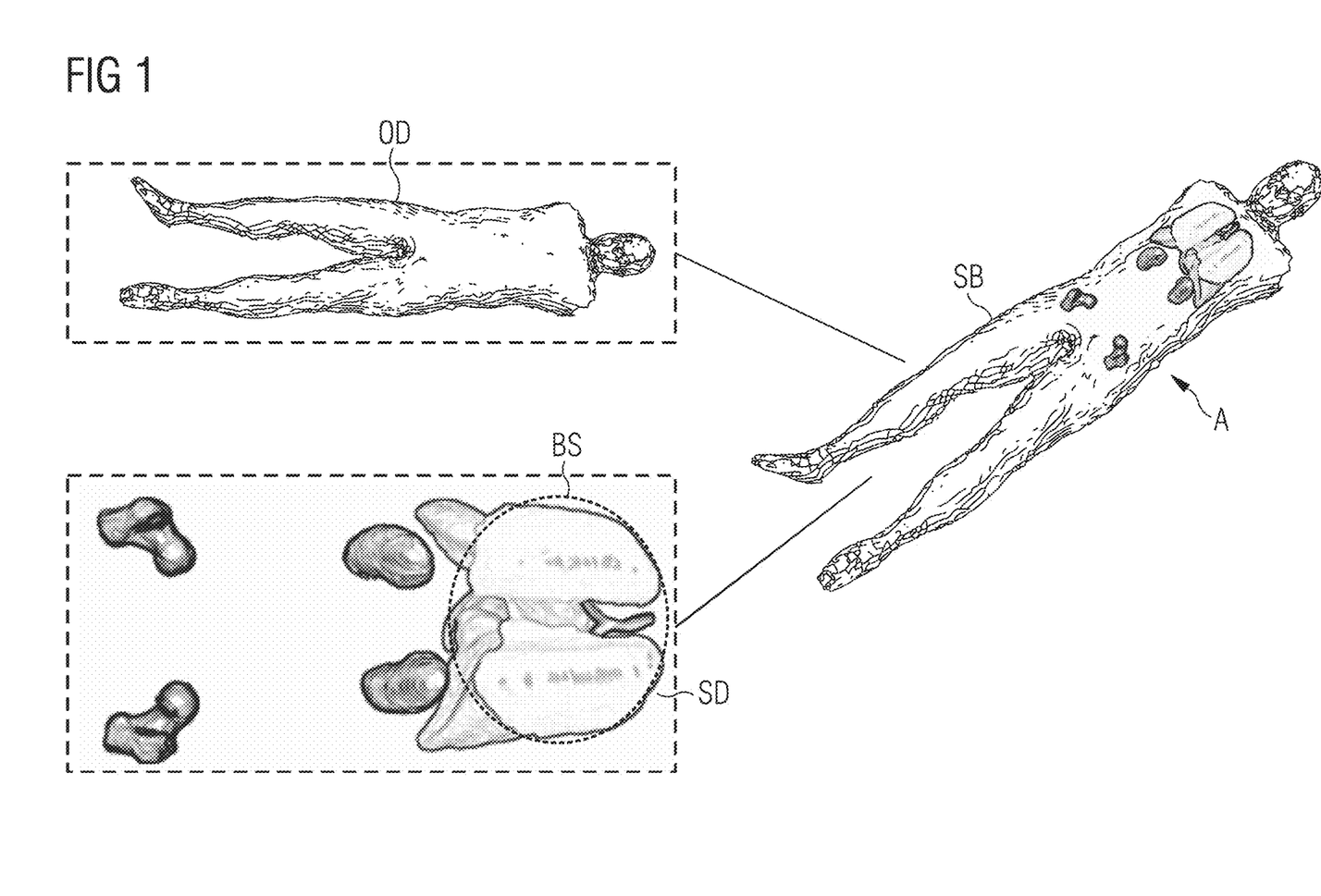
FIG. 1 shows a composition of a structure image in the form of an avatar.

FIG. 1 schematically shows a possible composition of a structure image SB in the form of an avatar A including surface data OD and structure data SD, BS.

Data relating to the surface of a person P is used as surface data OD. In the simplest case, this can be formed from a real 3D recording of a person. It is however useful in practice to calculate the surface data OD as average value data from the surfaces of a plurality of people, in order that the avatar A can be applied to as many people as possible. It is also conceivable to calculate the surface data OD from graphical models. In this case, the emphasis is on internal organs of the upper body, and therefore it is not necessary to represent the arms.

The structure data SD here is data from internal organs of a person. It can however also relate to bones, vessels, nerves or any other structures. In the simplest case, the structure data SD can likewise can be formed from a real recording of a person P, e.g. a CT recording. Here too, it is however useful in practice to calculate the structure data SD as average value data from recordings of a plurality of people, in order that the avatar A can be applied to as many different people as possible. It is likewise conceivable to calculate the structure data SD from graphical models.

In this example, the lungs are marked as particular structures BS, this being represented by a region surrounded by a broken line. These particular structures can be defined as structures of interest, for example, which would result in a selective recording of the lungs. However, it may also be the case that the particular structures are defined as structures of no interest, which would result in selective avoidance of a recording of the lungs.

The surface data OD and structure data SD may already be present in a single data record when the avatar A is produced. In the case shown here, the structure data SD (and therefore also BS) is registered with the surface data, e.g. to the extent that both data records were produced in similar coordinate systems and are mapped onto each other in accordance with the coordinates.

Figure 2:
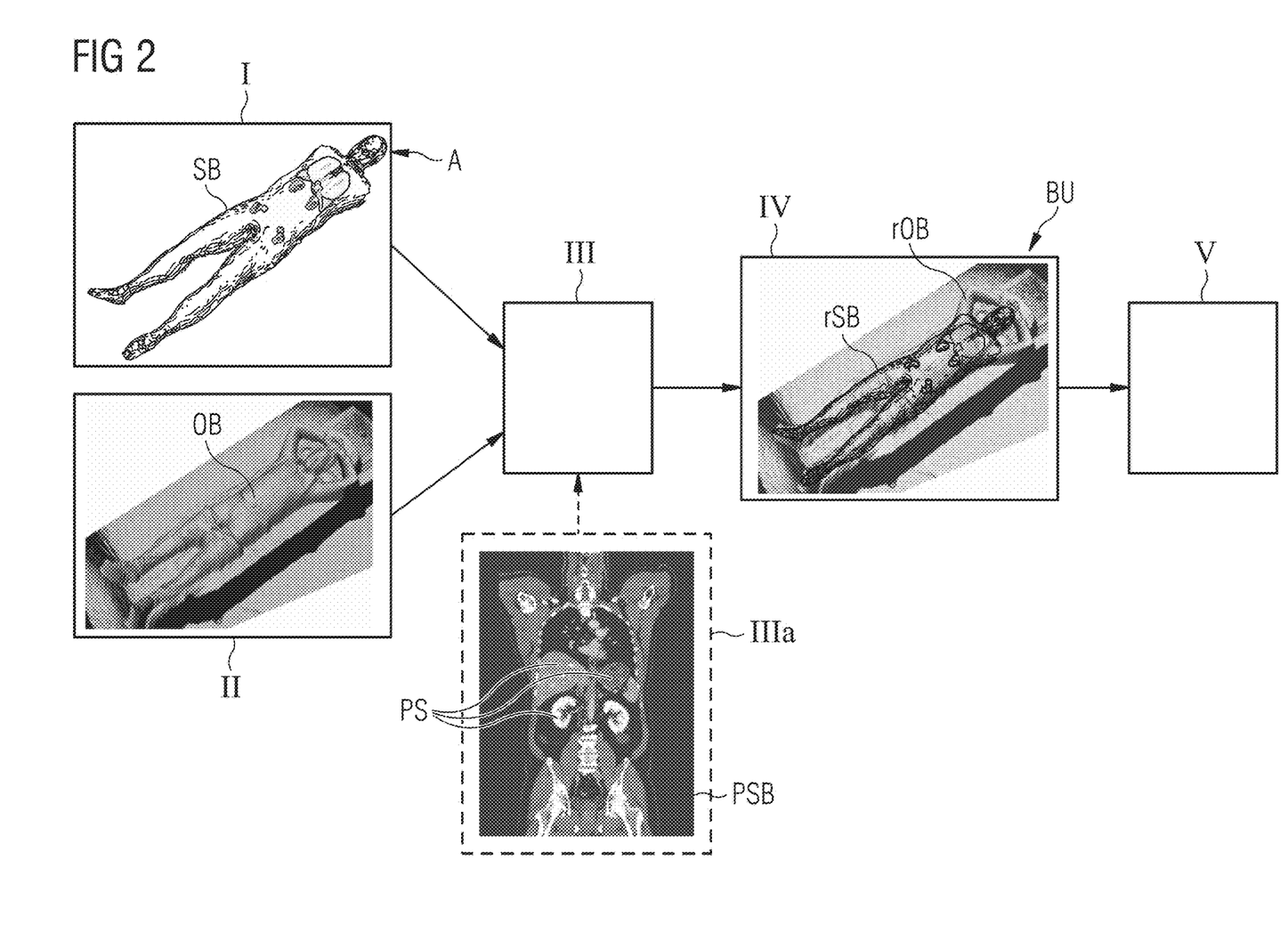
FIG. 2 shows a schematic representation of an embodiment of a method sequence.
Figure 4:
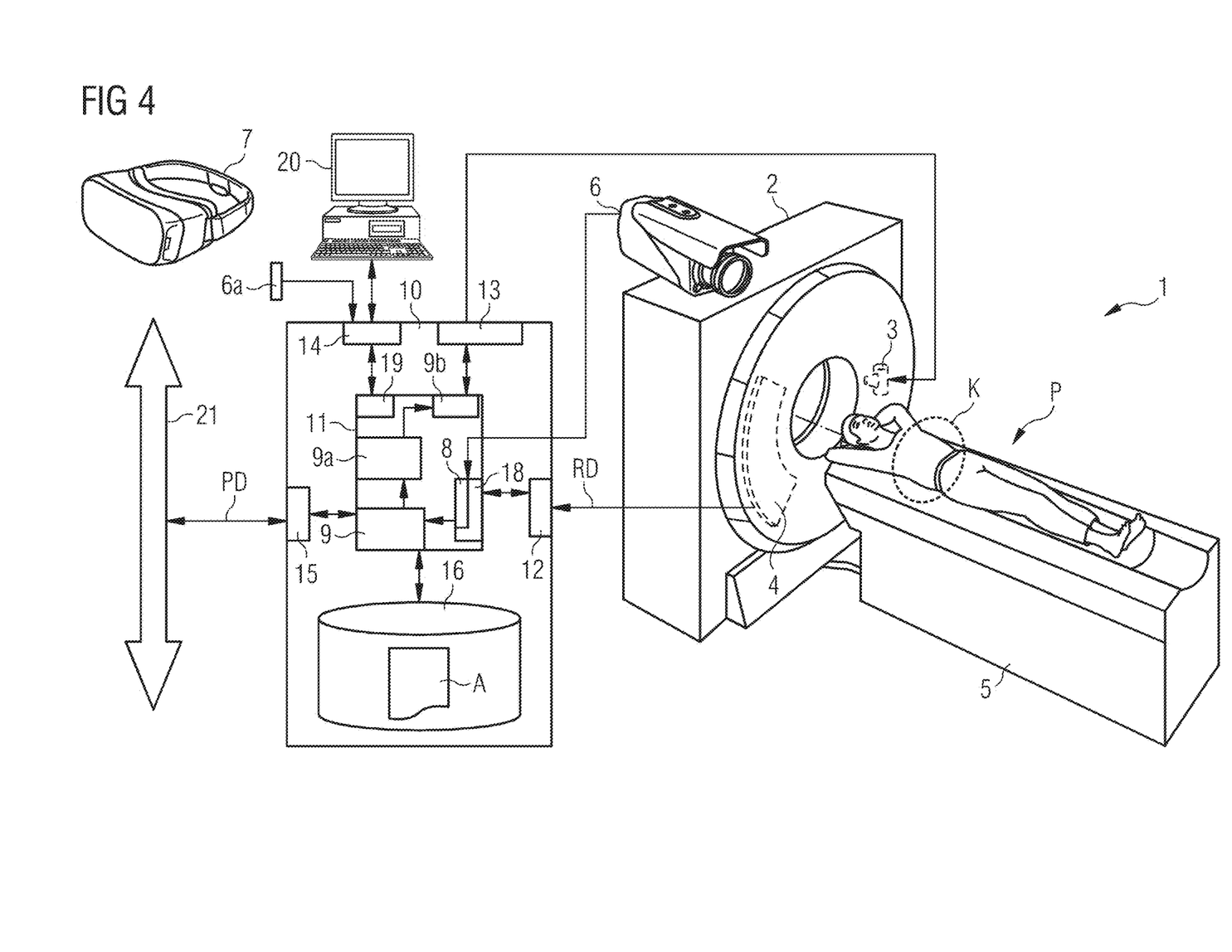
FIG. 4 shows a schematic representation of an example embodiment variant of an imaging system according to an embodiment of the invention and the way in which it functions.

FIG. 2 shows a schematic representation of a preferred method sequence for controlling a medical imaging system 1 as illustrated in e.g. FIG. 4 in the form of a block diagram.

In step I, a three-dimensional structure image SB is provided, which is an avatar A in this case. However, a previously produced CT recording of the patient could also be used here if such a recording is already available. As described above in relation to FIG. 1, the structure image SB comprises surface data OD relating to external contours and structure data SD relating to internal structures of a body region K of a patient P.

In step II, a recording of the body region K of the patient P is made using a camera system 6 while the patient P is situated in the medical imaging system 1 (cf. FIG. 4), and a three-dimensional surface image OB is produced from these recordings.

In step III, the surface image OB and the surface data OD of the structure image SB are registered in relation to each other. In this case, the structure data SD is registered together with the structure image SB, i.e. all graphical transformations which have to be performed for registration with the structure image are also applied correspondingly to the structure data SD.

In an optional step IIIa, a previously produced recording of the real structures of the patient, e.g. a scout scan, can be used as patient structure image PSB in order to register the structure data SD with the real internal structures PS of the patient independently of the surface data OD. This results in a better mapping of the structure data SD in the overlay image UB.

Figure 3:
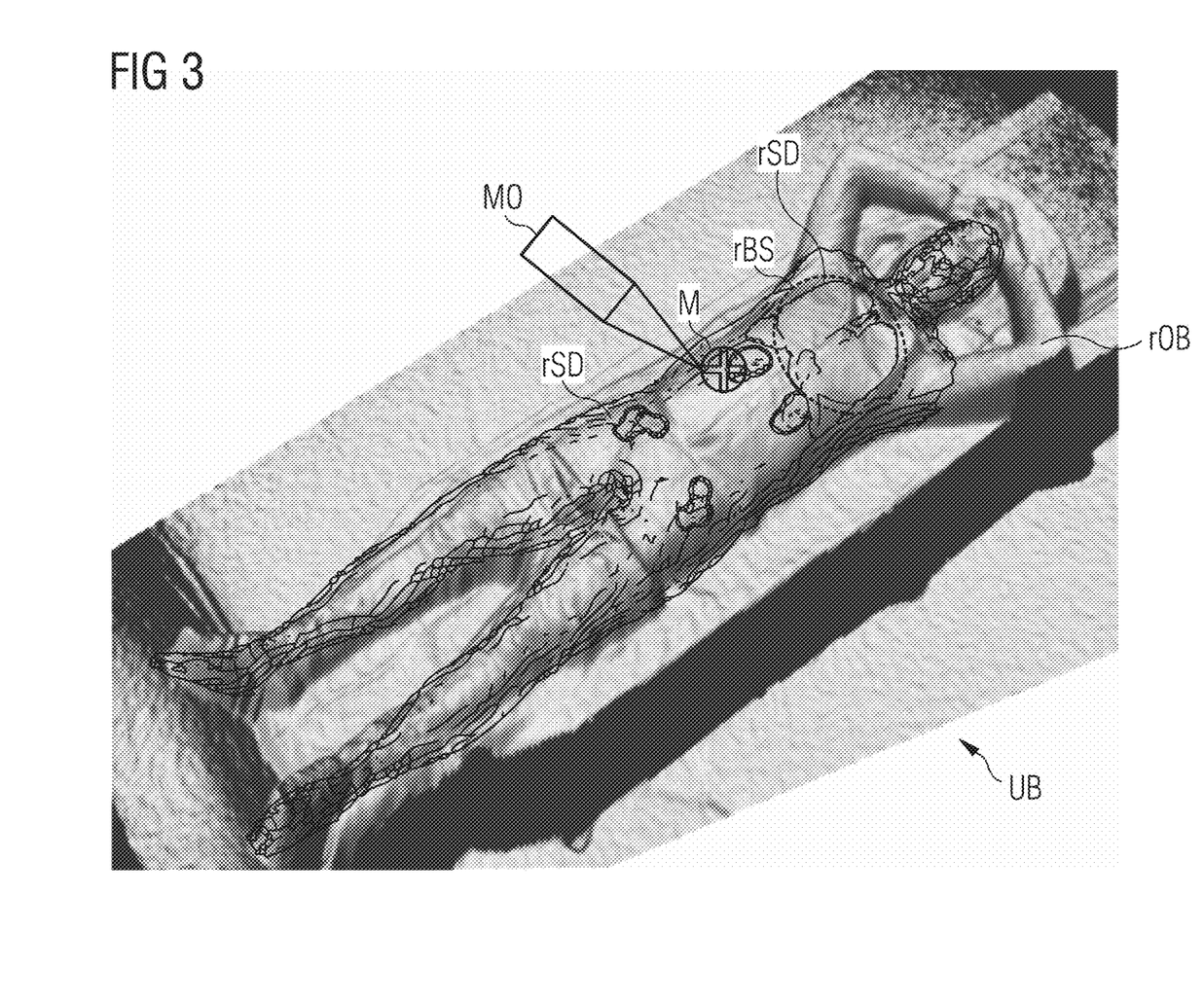
FIG. 3 shows an embodiment of an overlay image.

In step IV, an overlay image UB is produced as illustrated in greater detail in FIG. 3. The overlay image UB comprises at least part of the registered structure image rSB in the form of an overlay with the registered surface image rOB.

In step V, the medical imaging system 1 is controlled in such a way that the medical imaging system 1 records regions of the patient P on the basis of the registered structure data rSD in the overlay image. Since the overlay image reflects the real body view of the patient, the control can easily be effected in the coordinates system of the imaging system.

FIG. 3 perspectively shows a preferred overlay image UB including of a registered surface image rOB, a registered structure image rSB containing specific marked structures rBS, a virtual marking M and a virtual medical object MO.

FIG. 4 shows a schematic representation of a preferred control device 10 for controlling a medical imaging system 1, which is a computer tomography system 1 here. With regard to the control device 10, only those components which are essential or useful to the explanation of the invention are illustrated.

In a conventional manner, the computer tomography system 1 comprises a scanner 2 with a gantry in which an x-ray source 3 rotates and in each case radiographically penetrates a patient P, who is moved by way of a couch into a measurement space of the gantry, such that the radiation strikes a detector 4 that is situated opposite the x-ray source 3 in each case. A recording of a specific body region K is to be performed in this case.

A central component of the control device 10 here is a processor 11 on which various components are realized in the form of software modules. The control device 10 also has a terminal interface 14 allowing the attachment of a terminal 20 by which an operator can operate the control device 10 and therefore the computer tomography system 1. A further interface 15 is a network interface for connection to a data bus 21, in order to establish a connection to a Radiological Information System (RIS) or an image archiving system (PACS: Picture Archiving and Communication System). In this example, said interface 15 and data bus 21 are also used to send the data of the overlay image to a display device 7, specifically a VR or AR headset.

The scanner 2 can be activated by the control device 10 via a control interface 13, specifically e.g. the rotation speed of the gantry, the movement of the couch 5 and the x-ray source 3 itself are controlled. A clearly defined region can be recorded in this way. In particular, it is possible to control the slice orientation, the slice distance and/or the number of slices as described above.

The raw data RD is read out from the detector 4 via an acquisition interface 12. The raw data is reconstructed accordingly by way of an image reconstruction unit 18.

The control device 10 also has a storage unit 16 which can contain data for control purposes. In this example, the data relating to potential avatars A is also stored in this storage unit 16.

A further component on the processor 11 is a surface image production unit 8, which is designed to produce a three-dimensional surface image OB of the patient P, at least the body region K, from the images of a camera system 6. In this example, the surface image production unit 8 is part of the image reconstruction unit 18, or the functionality of the image reconstruction unit 18 has been supplemented by the functionality of the surface image production unit 8. The camera system is illustrated on the scanner for greater clarity here. In practice, it would advantageously be situated inside the scanner in order to continuously record the patient, possibly during a CT recording.

In the example shown, the surface image production unit 8 is also designed to receive and if applicable reconstruct raw data from the detector 1. In this way, the surface image production unit 8 can additionally provide a patient structure image PSB, e.g. from a scout scan, to the control device as shown as an option in FIG. 2.

A further component on the processor 11 is a registration unit 9. This registers the surface image OB and the surface data OD of the avatar A, and also the structure data SD of the avatar with the patient structure data PD if applicable, in relation to each other.

A further component on the processor 11 is an overlay image production unit 9a, which generates an overlay image from the registered surface image rOB and the registered structure image rSB together with the registered structure data rSD.

On the basis of the overlay image, or the registered structure image rSB together with the registered structure data rSD contained therein, it is possible to control the computer tomograph 1 in such a way that specific regions of the patient P can be selectively recorded or selectively not recorded. This can be realized by a recognition unit 9b, for example, which recognizes the registered structure data rSD, in particular marked particular structure data rBS, matches the coordinates thereof with the real coordinates of the patient (which is easy because the overlay image reflects the real coordinates of the patient) and, when controlling the device, always records the corresponding region if the particular structure data represents regions of interest, and does not record the corresponding region if the particular structure data represents regions of no interest.

As a preferred enhancement, the control device 10 additionally comprises an input unit 19 which is designed to record further control data from a user. The input unit 19 here is embodied as a gesture recognition unit which is capable of recognizing specified gestures of the user and translating these into control instructions. For this purpose, a camera 6a is additionally provided. The input unit 19 here receives data via the interface 14, which in turn receives data from the camera 6a. In addition, the input unit 19 can also receive data from the terminal 20. For example, the user could change, add or delete control parameters such as e.g. slice arrangements, etc., for a subsequent recording, said control parameters being visualized in real time in the VR or AR environment (i.e. in the "reality" which they see in an overlay image that is displayed by way of the VR or AR headset 7). For example, the user could push together or pull apart a slice stack using their hands (in order to reduce or increase the slice distances), rotate or otherwise reposition the stack in the space, or add new slices or delete slices.

In conclusion, it is again noted that the methods described in detail above and the device illustrated are merely exemplary embodiments that can be modified by a person skilled in the art in all variety of ways without thereby departing from the scope of the invention. Furthermore, use of the indefinite article "a" or "an" does not preclude the features concerned being present in multiples. Likewise, the terms "unit" and "module" do not preclude the components concerned including of a plurality of interworking subcomponents, which may also be physically distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. A method for controlling a medical imaging device of a medical imaging system, comprising:
providing a three-dimensional structure image including both surface data relating to external contours and structure data relating to internal structures of a body region;

recording the body region of a patient via a camera system while the patient is situated in or on a tomographic scanner of the medical imaging system, and producing a three-dimensional surface image during the recording;

registering, at least locally and as a structure image, the three-dimensional surface image in relation to the three-dimensional structure image;

marking the structure data as structures to be mapped by the medical imaging system, and structures not to be mapped by the medical imaging system;

producing an overlay image, the overlay image including at least part of the structure image registered including structure data of the three-dimensional structure image in a form of an overlay with at least one of the three-dimensional surface image and a real view of a corresponding part of the body region of the patient; and controlling at least movement of an x-ray source of the tomographic scanner of the medical imaging device to record body regions of the patient based upon an arrangement of the structure data registered in the overlay image.

2. The method as claimed in claim 1, wherein the structure image either
is based on a medical image recording of the body region of the patient or another patient; or
includes image data of a body region of an artificially produced avatar.

3. The method of claim 1, wherein before the registering, the three-dimensional structure image is automatically aligned and positioned according to the three-dimensional surface image or a corresponding transformation matrix is generated.

4. The method of claim 1, wherein a graphical transformation, applied to the external contours of the structure image for the registering, is applied to the structure data of the three-dimensional structure image, correspondingly.

5. The method of claim 1, wherein a patient structure image, featuring internal structures and information relating to a surface of the patient, is additionally recorded during the recording, via the medical imaging system, to supplement the registering, wherein the patient structure image is registered with the three-dimensional surface image, with respect of information relating to the surface of the patient, and wherein internal structure data of the structure image is additionally registered with corresponding internal structures of the patient structure image.

6. The method of claim 1, wherein the overlay image is displayed via a display device, wherein position and orientation of the display device are also determined, and wherein the overlay image is displayed such that a viewing angle from which the overlay image is displayed corresponds to that of the display device onto the patient.

7. The method of claim 1, wherein markers, generated automatically based upon specified data or produced manually, and at least one of navigation data and help data are also represented in the overlay image, wherein control of the medical imaging system takes place such that the medical imaging system records regions of the patient based upon arrangement of the structure data of the three-dimensional structure image and the markers in the overlay image.

8. The method of claim 1, wherein image data relating to a virtual medical object is represented in the overlay image, wherein at least one of orientation and position of the virtual medical object is changeable, and wherein the at least one of orientation and position of the overlay image is actively changeable by a user.

9. The method of claim 1, wherein the three-dimensional surface image is produced from images recorded via a 3D camera or via a number of 2D cameras interconnected for a purpose of recording a three-dimensional image.

10. A control device for controlling a medical imaging system, comprising:
a camera system to record at least a body region of a patient in a medical imaging system and to produce recordings;
a memory storing computer-readable instructions; and
one or more processors configured to execute the computer-readable instructions such that the one or more processors are configured to
provide a three-dimensional structure image including surface data relating to external contours and structure data relating to internal structures of the body region of the patient;
a camera system to record at least the body region of the patient in tomographic scanner of a medical imaging system and to produce recordings;
produce a three-dimensional surface image from the recordings;
at least locally register, as a structure image, the three-dimensional surface image in relation to the three-dimensional structure image;
mark the structure data as structures to be mapped by the medical imaging system, and structures not to be mapped by the medical imaging system;
produce an overlay image, the overlay image including at least part of the structure image registered including registered structure data in a form of an overlay with registered surface image or a real view of a corresponding part of a real body region of the patient, and
control movement of at least an x-ray source of the tomographic scanner of a medical imaging device of the medical imaging system to record regions of the patient based upon an arrangement of the structure data registered in the overlay image.

11. The control device of claim 10, further comprising at least one of:
a display device, and
an interface for the display device, at least one of the display device and the interface configured to display the overlay image.

12. A medical imaging system, comprising the control device of claim 10.

13. A non-transitory computer program product storing a computer program, directly loadable into a memory device of a control device, including program sections for executing the method of claim 1 when the computer program is executed in the control device.

14. A non-transitory computer-readable medium storing program sections, readable in and executable by a computer unit, to execute the method of claim 1 when the program sections are executed by the computer unit.

15. The method of claim 2, wherein before the registering, the three-dimensional structure image is automatically aligned and positioned according to the three-dimensional surface image or a corresponding transformation matrix is generated.

16. The method of claim 2, wherein a graphical transformation, applied to the external contours of the structure image for the registering, is applied to the structure data of the three-dimensional structure image, correspondingly.

17. The method of claim 6, wherein the display device is a Virtual Reality display device or an Augmented Reality display device.

18. The method of claim 6, wherein markers, generated automatically based upon specified data or produced manually, and at least one of navigation data and help data are also represented in the overlay image, wherein control of the medical imaging system takes place such that the medical imaging system records regions of the patient based upon arrangement of the structure data of the three-dimensional structure image and the markers in the overlay image.

19. The method of claim 6, wherein image data relating to a virtual medical object is represented in the overlay image, wherein at least one of orientation and position of the virtual medical object is changeable, and wherein the at least one of orientation and position of the overlay image is actively changeable by a user.

20. The method of claim 6, wherein the three-dimensional surface image is produced from images recorded via a 3D camera or via a number of 2D cameras interconnected for a purpose of recording a three-dimensional image, wherein at least one camera of the number of 2D cameras or the 3D camera, is at least one of integrated in the display device and positioned in the medical imaging system.

21. The method of claim 1, wherein the medical imaging device is one of a computer tomography device or magnetic resonance tomography device and the controlling includes controlling at least one of a rotation speed of a gantry of the medical imaging device, a movement of a couch of the medical imaging device, or an x-ray source of the medical imaging device.

22. The control device of claim 10, wherein the medical imaging device is one of a computer tomography device or magnetic resonance tomography device and the one or more processors are further configured to control at least one of a rotation speed of a gantry of the medical imaging device, a movement of a couch of the medical imaging device, or an x-ray source of the medical imaging device.

23. The method of claim 1, wherein the controlling includes irradiating only mapped structures.

24. The control device of claim 10, wherein the one or more processors are configured to control the x-ray source to irradiate only mapped structures.

* * * * *